United States Patent
Ko et al.

(10) Patent No.: US 10,016,179 B2
(45) Date of Patent: Jul. 10, 2018

(54) PROBE AND MANUFACTURING METHOD THEREOF

(71) Applicant: SAMSUNG MEDISON CO., LTD., Hongcheon-gun, Gangwon-do (KR)

(72) Inventors: Jong-Sun Ko, Seoul (KR); Ki Soo Kim, Seoul (KR); Hyun Phill Ko, Seongnam-si (KR); Yong Jae Kim, Gyeongju-si (KR); Saidmurod Akramov, Osan-si (KR); Jong Mok Lee, Yongin-si (KR)

(73) Assignee: Samsung Medison Co., Ltd., Hongcheon-gun, Gangwon-do (KR)

( * ) Notice: Subject to any disclaimer, the term of this patent is extended or adjusted under 35 U.S.C. 154(b) by 356 days.

(21) Appl. No.: 14/833,011

(22) Filed: Aug. 21, 2015

(65) Prior Publication Data
US 2016/0183916 A1 Jun. 30, 2016

(30) Foreign Application Priority Data
Dec. 26, 2014 (KR) .......... 10-2014-0190476

(51) Int. Cl.
| | |
|---|---|
| *H01L 41/09* | (2006.01) |
| *B06B 1/06* | (2006.01) |
| *A61B 8/00* | (2006.01) |
| *H01L 41/27* | (2013.01) |
| *H01L 41/113* | (2006.01) |
| *G10K 11/02* | (2006.01) |

(52) U.S. Cl.
CPC .......... *A61B 8/4444* (2013.01); *A61B 8/4272* (2013.01); *B06B 1/067* (2013.01); *G10K 11/02* (2013.01); *H01L 41/09* (2013.01); *H01L 41/113* (2013.01); *H01L 41/27* (2013.01)

(58) Field of Classification Search
CPC ....... B06B 1/06; B06B 1/0603; B06B 1/0644; B06B 1/0677
USPC ......................... 310/322, 334, 335
See application file for complete search history.

(56) References Cited

U.S. PATENT DOCUMENTS

| | | | |
|---|---|---|---|
| 5,577,507 | A | 11/1996 | Snyder et al. |
| 5,820,564 | A | 10/1998 | Slayton et al. |

(Continued)

FOREIGN PATENT DOCUMENTS

| | | |
|---|---|---|
| EP | 2401966 A1 | 1/2012 |
| EP | 2 638 861 A1 | 9/2013 |

OTHER PUBLICATIONS

Extended European Search Report issued in Application No. 15163036.5 dated Jun. 6, 2016.

(Continued)

*Primary Examiner* — Derek Rosenau
(74) *Attorney, Agent, or Firm* — McDermott Will & Emery LLP

(57) ABSTRACT

A probe includes: a piezoelectric layer to generate ultrasonic waves, a backing layer to absorb ultrasonic waves generated at the piezoelectric layer and proceeding toward a rear, a reflective layer occupying an area smaller than an area of the piezoelectric layer and provided in between the piezoelectric layer and the backing layer to amplify the ultrasonic waves generated at the piezoelectric layer, and a lens layer to focus the ultrasonic waves proceeding toward a front of the piezoelectric layer at a certain point.

9 Claims, 6 Drawing Sheets

(56) References Cited

U.S. PATENT DOCUMENTS

2003/0013967 A1    1/2003  Savord et al.
2010/0066207 A1*   3/2010  Saito .................. A61B 8/4281
                                                        310/335

OTHER PUBLICATIONS

European Office Action issued in Application No. 15 163 036.5 dated Feb. 13, 2018.

* cited by examiner

US 10,016,179 B2

PROBE AND MANUFACTURING METHOD THEREOF

CROSS-REFERENCE TO RELATED APPLICATION

This application claims the priority benefit of Korean Patent Application No. 10-2014-0190476, filed on Dec. 26, 2014, in the Korean Intellectual Property Office, the disclosure of which is incorporated herein by reference.

BACKGROUND

1. Field

Apparatuses and methods consistent with exemplary embodiments relate to a probe provided to transmit/receive ultrasonic waves and a manufacturing method thereof.

2. Description of the Related Art

An ultrasonic imaging apparatus is an apparatus configured to transmit ultrasonic waves toward a target portion of an inside a subject from a surface of the subject, and non-invasively obtain cross sections of soft tissues or images related to blood flow by receiving reflected echo ultrasonic waves.

The ultrasonic imaging apparatus, when compared to other image diagnosis apparatus such as an x-ray apparatus, a CT Scanner (Computerized Tomography Scanner), a MRI (Magnetic Resonance Imaging) apparatus, or a nuclear medicine diagnosis apparatus, is provided in a small size thereof and less expensive, and is capable of displaying diagnostic images of an inside in real time. In addition, as no radiation exposure is present, the ultrasonic imaging apparatus is provided with higher level of safety. Therefore, the ultrasonic imaging apparatus is widely used in diagnoses of a heart and abdomen, in urology, as well as in gynecologic diagnosis.

The ultrasonic imaging apparatus is configured to transmit ultrasonic waves toward a subject as to obtain ultrasonic images of the subject, and includes a probe to receive echo ultrasonic waved that are reflected from the subject.

SUMMARY

One or more exemplary embodiments provide a probe configured to form a narrow bandwidth in a short-distance domain while focusing length of ultrasonic waves is reduced as a reflective layer occupying an area smaller than that of a piezoelectric layer, and a manufacturing method thereof.

It is another aspect of the present disclosure to provide a probe capable of physically carry out an apodization as to improve quality of ultrasonic images, and a manufacturing method thereof.

Additional aspects of the disclosure will be set forth in part in the description which follows and, in part, will be obvious from the description, or may be learned by practice of the exemplary embodiments.

In accordance with a aspect of an exemplary embodiment, a probe includes a piezoelectric layer, a backing layer, a reflective layer, and a lens layer. The piezoelectric layer may generate ultrasonic waves. The backing layer may absorb ultrasonic waves generated at the piezoelectric layer and proceeding toward a rear. The reflective layer may occupy an area smaller than an area of the piezoelectric layer and provided in between the piezoelectric layer and the backing layer to amplify the ultrasonic waves generated at the piezoelectric layer. The lens layer may focus the ultrasonic waves proceeding toward a front of the piezoelectric layer at a certain point.

The reflective layer may be provided at a central portion in an elevation direction of the probe.

The reflective layer may be formed of material having am acoustic impedance higher than an acoustic impedance of the piezoelectric layer.

The reflective layer may be formed of material having an acoustic impedance 1.5 times higher than an acoustic impedance of the acoustic impedance of the piezoelectric layer.

The probe may further include a matching layer to reduce a difference of acoustic impedances between the piezoelectric layer and a subject.

The reflective layer may be provided at a depressed surface of the backing layer.

The piezoelectric layer and the reflective layer may be provided at the depressed surface of the backing layer.

The reflective layer may occupy a shorter length in the elevation direction than a length of the piezoelectric layer.

The piezoelectric layer, the backing layer, the reflective layer, and the lens layer each may be provided with both end portions thereof symmetrical to each other about a central portion of the probe having a length in the elevation direction.

In accordance with another aspect of the present disclosure, a manufacturing method of a probe includes providing a backing layer, providing a reflective layer, providing a piezoelectric layer occupying an area larger than an area of the reflective layer, and providing a lens layer to focus ultrasonic waves proceeding toward a front of the piezoelectric layer at a certain point.

The manufacturing method may further include forming a first depressed surface, prior to providing the reflective layer, by removing the backing layer, wherein the providing of the reflective layer may include stacking the reflective layer at the first depressed surface.

The manufacturing method may further include forming a second depressed surface, prior to the providing of the piezoelectric layer, by removing the backing layer, wherein the providing of the piezoelectric layer may include stacking the piezoelectric layer at the second depressed surface.

The providing of the piezoelectric layer may include stacking the piezoelectric layer at an upper surface of the reflective layer and at an upper surface of a non-depressed surface of the backing layer.

The providing of the reflective layer may include providing the reflective layer at a central portion of the probe in an elevation direction of the probe.

The manufacturing method may further include providing a matching layer, prior to the providing of the lens layer, to reduce a difference of acoustic impedances between the piezoelectric layer and a subject.

The providing of the piezoelectric layer may include providing the piezoelectric layer occupying a longer length in the elevation direction than a length of the reflective layer.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
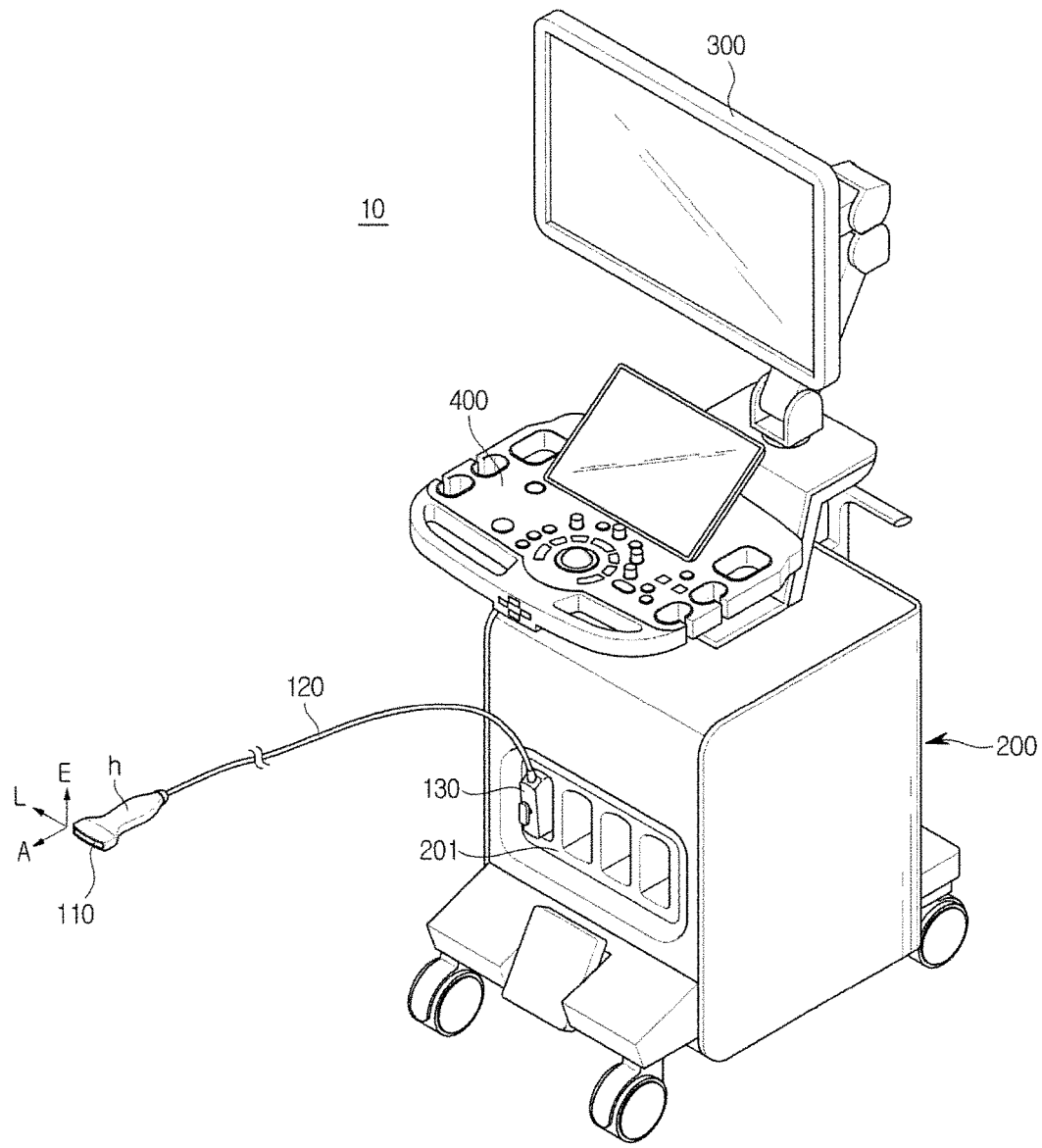
FIG. 1 is a view of an ultrasonic imaging apparatus in accordance with an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail Reference will now be made in detail to the exemplary embodiments, examples of which are illustrated in the accompanying drawings, wherein like reference numerals refer to like elements throughout.

Figure 2:
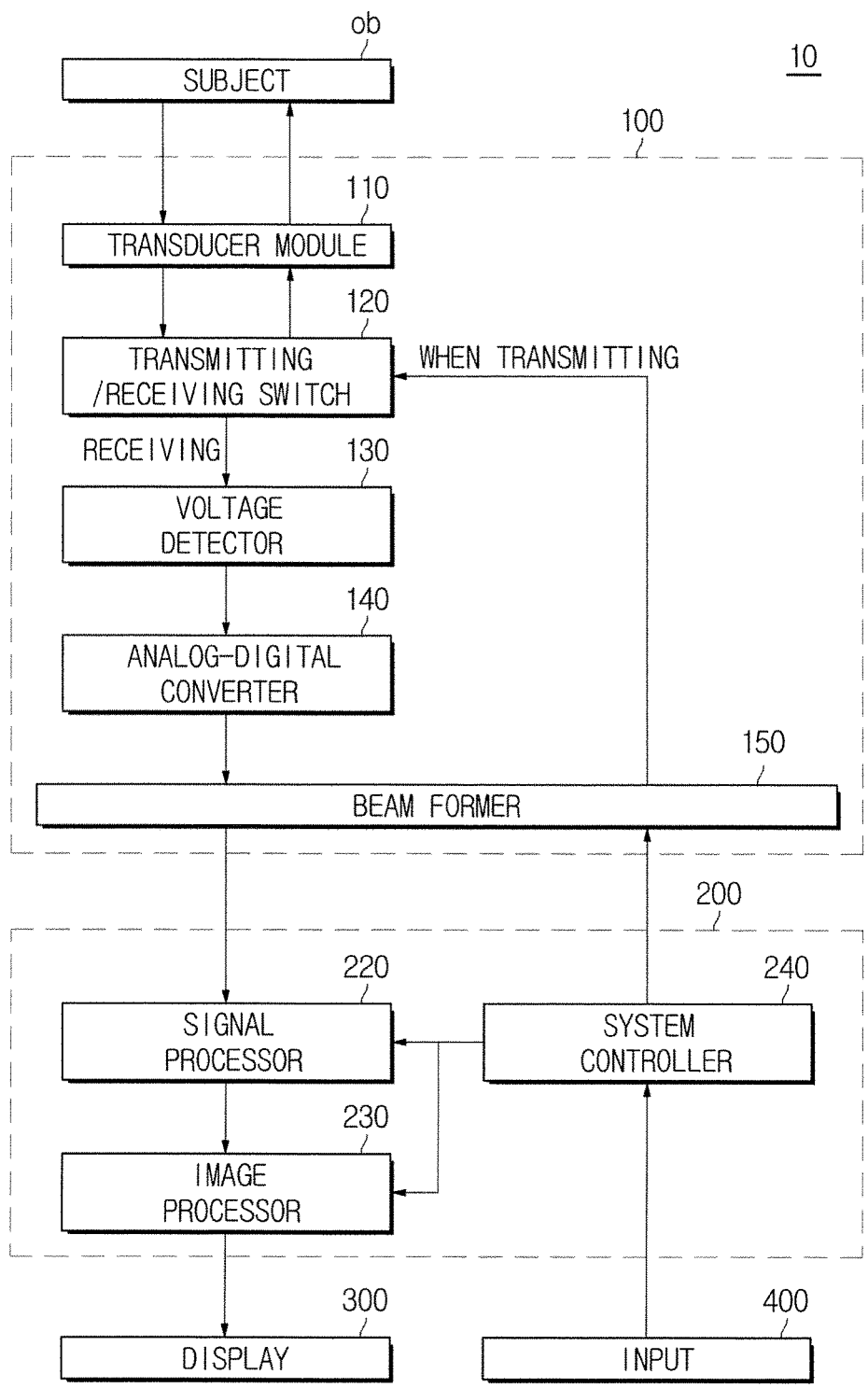
FIG. 2 is a block diagram of the ultrasonic imaging apparatus in accordance with an exemplary embodiment.

FIG. 1 is a view of an ultrasonic imaging apparatus in accordance with one exemplary embodiment, and FIG. 2 is a block diagram of the ultrasonic imaging apparatus in accordance with one exemplary embodiment.

Referring to FIG. 1, an ultrasonic imaging apparatus 10 includes a probe 100 and a body 200, and the body 200 is connected to the probe 100, and may be a work station provided with a display 300 and an input apparatus 400.

Hereinafter, the descriptions will be provided first with respect to the probe 100.

The probe 100 includes a transducer module 110 provided at an inside a housing h to transmit ultrasonic waves toward a subject, configured to receive echo ultrasonic waves that are reflected from the subject, and configured to reciprocally convert electrical signals and the ultrasonic waves, a male connector physically connected to a female connector and configured to transmit/receive signals with respect to the body 200, and a cable connecting the male connector and the transducer module 110.

Here, the subject may be a human being or a body of an animal, or tissue at an inside a body, such as blood vessels, bones, or muscles, but is not limited hereto, and the subject may be referred to any entity provided with an inside structure thereof displayed as an image by use of the ultrasonic imaging apparatus 10.

A diagnostic mode may be one of an A-mode (Amplitude mode), a B-mode (Brightness mode), a D-mode (Doppler mode), an E-mode (Elastography mode), a M-mode (Motion mode), or a CPS-mode (cadence pulse sequencing mode), but is not limited hereto.

The echo ultrasonic waves are referred to as the ultrasonic waves that are reflected from the subject at which the ultrasonic waves are transmitted, and is provided with various frequency bands or energy strength that are configured to generate various ultrasonic images according to the diagnostic mode.

The transducer module 110 may be able to generate ultrasonic waves according to an applied alternating current power. In detail, the transducer 110 may be able to receive the alternating current power from an outside power supplying apparatus or an inside electrical storage apparatus, for example, a battery. An oscillator of the transducer module 110 may be able to generate ultrasonic waves as the oscillator is vibrated according to the supplied alternating current power.

The three directions that are provided to form perpendicular angles while having a center of the transducer module 110 as a center may be defined as an axis direction A, a lateral direction L, and an elevation direction E. In detail, the direction in which ultrasonic waves are transmitted is defined as the axis direction A, the direction in which the transducer module 110 is provided to generate heat is defined as the lateral direction L, and one remaining direction provided to be perpendicular with respect to the axis direction A and the lateral direction L is defined as the elevation direction E.

As for the transducer module 110, various types of ultrasonic transducer modules, for example, a Magnetostrictive Ultrasonic Transducer provided to use magnetostrictive effect of a magnetic substance, a Piezoelectric Ultrasonic Transducer provided to use piezoelectric effect of a piezoelectric substance, a Capacitive Micromachined Ultrasonic Transducer (cMUT) provided to transmit/receive ultrasonic waves by use of vibrations of micro-processed hundreds or thousands of thin films, and a piezoelectric micromachined ultrasonic transducer (pMUT), may be used.

The cable provided with one end thereof is connected to the transducer module 110, and provided with the other end thereof connected to the male connector, and thus connecting the transducer module 110 and the male connector.

The male connector 130 is connected to the other end of the cable, and may be physically connected to the female connector 201 of the body 200.

The male connector 130 as such may be able to deliver electrical signals generated by use of the transducer module 110 to the physically connected female connector 201, or may be able to receive control signals generated by use of the body 200 from the female connector 201.

However, in a case when the probe 100 is implemented in the form of the wireless probe 100, the cable and the connector as such may be omitted, and the probe 100 and the body 200 may be able to transmit/receive signals through a separate wireless communication module (not shown) included in the probe 100, and thus the shape of the probe 100 illustrated on FIG. 1 is not limited hereto.

In addition, referring to FIG. 2, the probe 100 further includes a beam former 150 provided at an inside the housing h, a transmitting/receiving switch 120, a voltage detector 130, and an analog-digital converter 140.

The transmitting/receiving switch 120 is configured to convert modes into a transmitting mode at the time of radiating ultrasonic waves or into a receiving mode at the time of receiving ultrasonic waves, according to the control signal of a system controller 240.

The voltage detector 130 is provided to detect the current that is output from the transducer module 110. The voltage detector 130, for example, may be implemented as an amplifier to amplify voltage according to the output current.

Other than the above, the voltage detector 130 may further include a pre-amplifier to amplify micro-sized analog signals, and thus as the pre-amplifier, a low noise amplifier (LNA) may be used.

In addition, the voltage detector 130 may further include a variable gain amplifier (VGA: not shown) to control gain values according to input signals. At this time, a Time Gain Compensation (TGC) provided to compensate the gain obtained with respect to the focusing point or with respect to the distance from the focusing point by use of the variable gain amplifier may be used, but is not limited hereto.

The analog-digital converter 140 is provided to convert the output analog voltage from the voltage detector 130 into digital signals.

On FIG. 2, the digital signals converted at the analog-digital converter 140 are illustrated to be input at the beam former 150. However, in the contrary, the analog signals delayed at the beam former 150 may be input at the analog-digital converter 140, and thus the order of such is not limited hereto.

In addition, on FIG. 2, the analog-digital converter 140 is illustrated to be provided at an inside the probe 100, but is not limited hereto, and the analog-digital converter 140 may be provided at an inside the body 200. In the case as such, the analog-digital converter 140 may be able to convert the analog signals focused by use of an adder into digital signals.

The beam former 150 is an apparatus configured to provide proper delayed time at the ultrasonic waves being transmitted or at the echo ultrasonic waves being received, so that the ultrasonic waves generated at the transducer module 110 are focused at one target point of a subject at the desired identical time or that the echo ultrasonic waves reflected and returning from the one target point of the subject may overcome the time difference in reaching at the transducer module 110.

With respect to the ultrasonic imaging apparatus 10 illustrated on FIG. 2, as described above, the beam former 150 may be included at the probe 100 that is regarded as a front end, or may be included at the body 200 that is regarded as a back end. Since no limitation is provided with respect to the above in the embodiment of the beam former 150, the entirety or the part of the components of the beam former 150 may be included at the front end or the back end.

The body 200 is an apparatus configured control the probe 100 or to store the components that are needed to generate ultrasonic images on the basis of the signals received from the probe 100, and may be connected to the probe 100 through the cable.

Hereinafter, a signal processor 220, an image processor 230, and the system controlloer 240 included at the body 200 will be described, and the descriptions will be provided with respect to the display 300 and the input unit 400.

The signal processor 220 is provided to convert the focused digital signals that are received from the probe 100 into a form that is proper for image processing. For example, the signal processor 220 may be able to perform a filtering to remove noise signals at outside the desired frequency band.

In addition, the signal processor 220 may be implemented in the form of a DSP (Digital Signal Processor), and may be able to generate ultrasonic images by performing an envelope detecting process configured to detect the size of echo ultrasonic waves on the basis of the focused digital signals.

The image processor 230 is provided to generate images so that an inside a subject, for example, the inside a human body, may be visually checked by a user, for example, a doctor or a patient, on the basis of the ultrasonic image data that is generated at the signal processor 220.

The image processor 230 is provided to deliver the ultrasonic image that is generated by use of the ultrasonic image data to the display 300.

In addition, the image processor 230 may further be able to perform additional image processing separately with respect to ultrasonic images according to the embodiment. For example, the image processor 230 may further be able to process a post processing, such as calibration or readjustment of contrast, brightness, and sharpness of the ultrasonic images.

The additional image processing of the image processor 230 as such may be performed according to a predetermined setting, or may be performed according to an instruction or a command of a user being input through the input apparatus 400.

The system controlloer 240 is provided to control overall motions of the ultrasonic imaging apparatus 10. For example, the system controlloer 240 is provided to control motions of the signal processor 220, the image processor 230, the probe 100, and the display 300.

In accordance with the embodiment, the system controlloer 240 may be able to control the motions of the ultrasonic imaging apparatus 10 according to a predetermined setting, or may be able to control the motions of the ultrasonic imaging apparatus 10 after generating a predetermined control command according to an instruction or a command of a user being input though the input apparatus 400.

The system controlloer 240 may include a processor, a ROM at which a control program configured to control the ultrasonic imaging apparatus 10 is stored, and a RAM configured to store the signals or the ultrasonic image data being input from the probe 100 of the ultrasonic imaging apparatus 10 or the input apparatus 400 or being used as a storage domain that corresponds to various tasks being performed at the ultrasonic imaging apparatus 10.

In addition, the system controlloer 240 may include a graphic processing board, which is provided with the processor, the RAM, or the ROM having, at a separate circuit board that is electrically connected with the system controlloer 240.

The processor, the RAM, and the ROM may be reciprocally connected through an inside bus.

In addition, the system controlloer 240 may be used as the terminology referring to the components including the processor, the RAM, and the ROM.

In addition, the system controlloer 240 may be used as the terminology referring to the components including the processor, the RAM, the ROM, and a processing board.

The at least one female connector 201 (FIG. 1) is provided at the body 200, and the female connector 201 may be able to be connected to the probe 100 through the cable and the male connector 130.

The display 300 is provided to display the ultrasonic images generated at the imaging processor 230, so that a user may be able to visually check the structure or the tissue of an inside a subject.

The input apparatus 400 is input with a predetermined instruction or a command from a user as to control the ultrasonic imaging apparatus 10. The input apparatus 400 may include a user interlace, for example, a keyboard, a mouse, a trackball, a touch screen, or a paddle.

Hereinafter, the detailed structure of the transducer module in accordance with one embodiment of the present disclosure will be described in detail by referring to FIG. 3 and FIG. 4.

Figure 3:
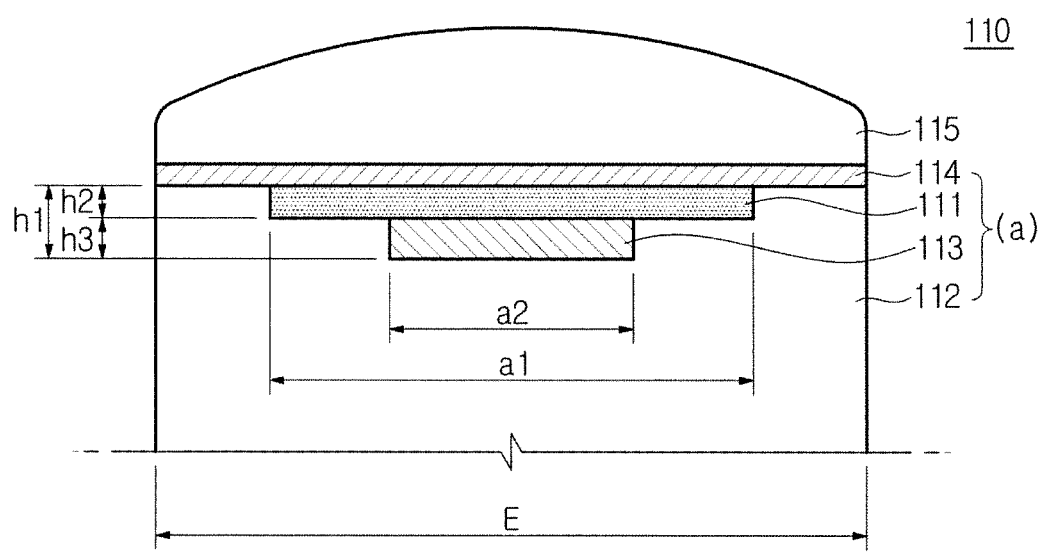
FIG. 3 is a side view of a transducer module in an elevation direction in accordance with an exemplary embodiment.
Figure 4:
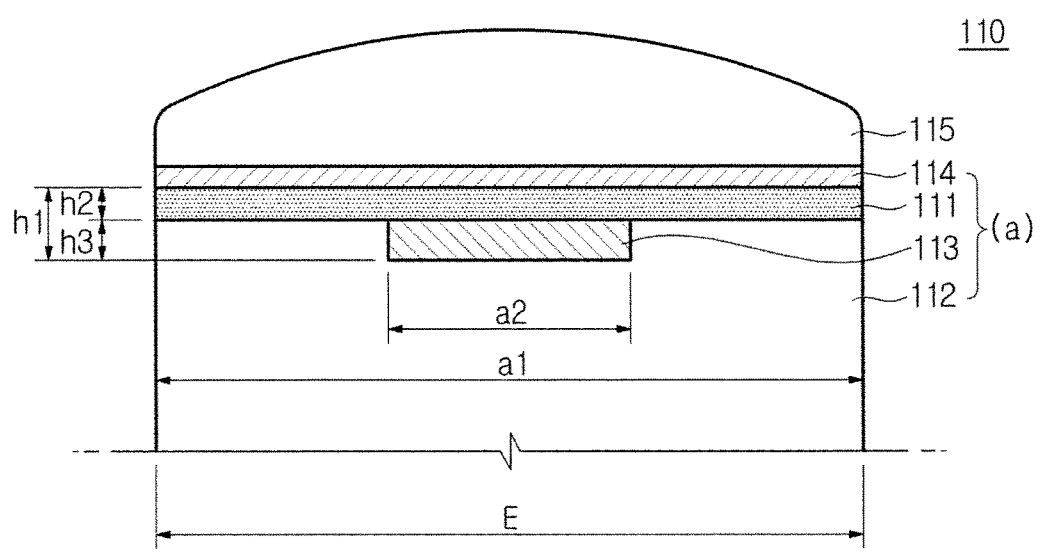
FIG. 4 is a side view of the transducer module in an elevation direction in accordance with another exemplary embodiment.

FIG. 3 is a side view of the transducer module in the elevation direction in accordance with one exemplary embodiment, and FIG. 4 is a side view of the transducer module in the elevation direction in accordance with another exemplary embodiment.

Referring to FIG. 3 and FIG. 4, the transducer module 110 in accordance with one embodiment of the present disclosure includes an acoustic module a structure having a piezoelectric layer 111, a backing layer 112 provided at a lower surface of the piezoelectric layer 111, a reflective layer 113 provided in between the backing layer 112 and the piezoelectric layer 111, and a matching layer 114 provided at an upper surface of the piezoelectric layer 111, and a lens layer 115 to focus the ultrasonic waves proceeding toward a front of the piezoelectric layer 111 to a certain point.

The piezoelectric layer 111 is provided with piezoelectric material to generate ultrasonic waves by converting electrical signals into mechanical vibration when the electrical signals are applied.

When mechanical pressure is applied at predetermined material, a voltage is generated, and when the voltage is applied, an effect of mechanical deformation is occurred, and the effect as such is referred to a piezoelectric effect or an inverse piezoelectric effect, and the material having the effect as such is referred to as piezoelectric material.

That is, piezoelectric material is referred to as material to convert electrical energy into mechanical vibration energy, and to convert mechanical vibration energy into electrical energy.

The piezoelectric material may include a PZMT single crystal made by use of a solid solution of a ceramic of lead zirconate titanate (PZT), magnesium niobate and titanate, and a PZMT single crystal made by use of a solid solution of zinc niobate and titanate.

The piezoelectric layer 111 is provided to transmit mechanical vibration energy as ultrasonic waves toward a direction in which the lens is provided (hereinafter is referred to as a front) and toward a direction in which the backing layer 112 is provided (hereinafter is referred to as a rear).

The piezoelectric layer 111 may be arranged in a single layer or a stacked structure having a plurality of layers.

The backing layer 112 is installed at a lower surface of the piezoelectric layer 111, and by absorbing the ultrasonic waves generated from the piezoelectric layer 111 and proceeding toward the rear, the proceeding of the ultrasonic waves toward the rear of the piezoelectric layer 111 is prevented. Thus, an occurrence of a distortion of an image may be prevented.

The backing layer 112 may be provided with small acoustic impedance with respect to the piezoelectric layer 111. For example, the backing layer 112 may be structured by use of material having acoustic impedance between about 2 MRayl and about 5 MRayl.

The backing layer 112 may be manufactured in a plurality of layers as to improve reduction or shielding effect of ultrasonic waves.

The reflective layer 113 is provided in between the backing layer 112 and the piezoelectric layer 111 as to amplify the vibration energy generated at the piezoelectric layer 111.

The reflective layer 113 in accordance with one embodiment of the present disclosure may be provided to occupy a small area with respect to the piezoelectric layer 111 at a central portion of the piezoelectric layer 111. In the case as such, the reflective layer 113 is provided to amplify the vibration energy transmitted from the central portion of the piezoelectric layer 111, and thus the strength of the acoustic pressure of the ultrasonic waves transmitted from the central portion may be increased.

The reflective layer 113 in accordance with another embodiment of the present disclosure may be provided to occupy a short length in the elevation direction E, for example, less than about 90%, from the central portion of the piezoelectric layer 111 with respect to the piezoelectric layer 111 while having the elevation direction E as a center. In the case as such, the reflective layer 113, by reflecting the vibration energy, which is transmitted toward the rear from the central portion in the elevation direction E of the piezoelectric layer 111, toward the front again, the ultrasonic waves transmitted from the piezoelectric layer 111 may be amplified. That is, the reflective layer 113 may be able to increase the acoustic strength of the ultrasonic waves, which are transmitted from the central portion of the piezoelectric layer 111 while having the elevation direction E as a center.

The reflective layer 113 may be provided with large acoustic impedance with respect to the piezoelectric layer 111. For example, the reflective layer 113 may be provided with material having the acoustic impedance that is about 1.5 times greater than the acoustic impedance of the piezoelectric layer 111, for example, between about 50 MRayl and about 150 MRayl.

In accordance with one embodiment of the present disclosure, the piezoelectric layer 111 and the reflective layer 113 may be provided at a depressed surface of the backing layer 112.

In detail, referring to FIG. 3, the reflective layer 113 may be formed at the depressed surface of the backing layer 112 formed by partially removing the backing layer 112, and after forming the reflective layer 113, the piezoelectric layer 111 may be formed at the depressed surface of the backing layer 112 which is formed by partially removing the backing layer 112 again. Hereinafter, the depressed surface of the backing layer 112 at which the reflective layer 113 is formed is referred to as a first depressed surface, and the depressed surface of the backing layer 112 at which the piezoelectric layer 111 is formed is referred to as a second depressed surface.

In the case as the above, the length a2 of the elevation direction E of the reflective layer 113 provided at the first depressed surface is provided to be shorter with respect to the length a1 of the elevation direction E of the piezoelectric layer 111 provided at the second depressed surface.

In addition, the height of the depressed surface of the backing layer 112 may be identical with respect to the sum h1 of a height h3 of the reflective layer 113 and a height h2 of the piezoelectric layer 111.

In accordance with another embodiment of the present disclosure, the reflective layer 113 is provided at the depressed surface of the backing layer 112, and the piezoelectric layer 111 may be provided at upper surfaces of the reflective layer 113 and the backing layer 112.

In detail, referring to FIG. 4, the reflective layer 113 may be formed at the depressed surface of the backing layer 112 formed by partially removing the backing layer 112, and after forming the reflective layer 113, the piezoelectric layer 111 may be formed by stacking the piezoelectric layers 111 at an upper surface of the reflective layer 113.

In the case as the above, the length a2 of the elevation direction E of the reflective layer 113 provided at the depressed surface of the backing layer 112 is provided to be shorter with respect to the length a1 of the elevation direction E of the piezoelectric layer 111.

In addition, the height of the backing layer 112 may be identical with respect to the height h3 of the reflective layer 113.

Other than the above, the height of the depressed surface of the backing layer may be varied depending on the structure provided at an inside the backing layer 112.

The matching layer 114 is provided at an upper surface of the piezoelectric layer 111. The matching layer 114 may be able to efficiently deliver the ultrasonic waves generated at the piezoelectric layer 111, as the acoustic impedances of the piezoelectric layer 111 and a subject are matched by reducing the difference of the acoustic impedance between the piezoelectric layer 111 and the subject.

For the above, the matching layer 114 may be provided with material having large acoustic impedance with respect to the subject and having small acoustic impedance with respect to the piezoelectric layer 111.

The matching layer 114 may be formed by use of glass or resin material.

In addition, the matching layer 114 may be provided in the plurality of matching layers 114 so that the acoustic impedance may be gradually changed from piezoelectric layer 111 toward a subject, and the material of the each of the plurality of matching layers 114 may be provided to be different with respect to each other.

The piezoelectric layer 111 and the matching layer 114 may be processed in the form of a two-dimensional array having the shape of a matrix by use of a dicing processing, and may be processed in the form of a one-dimensional array.

The lens layer 115 may be provided to cover an upper surface and a side surface of a protective layer. The lens layer 115 is configured to focus the ultrasonic waves proceeding toward the front of the transducer module 110 at a certain point.

The lens layer 115 may be provided by use of material having strong wear resistance and high ultrasonic wave frequency as to focus ultrasonic waves and perform a role to protect an acoustic module, in detail, a transducer module 110 layer. The lens layer 115 may be provided with the shape that is convex toward a radiating direction of ultrasonic waves as to focus the ultrasonic waves, and in a case when acoustic speed is slower than a human body, the lens layer 115 may be provided with a concave shape.

The left side portion and the right side portion, that is, the both end portions, of the piezoelectric layer 111, backing layer 112, the reflective layer 113, the matching layer 114, and the lens layer 115 may be symmetrically formed with respect to each other while having a central portion of the probe 100 having a length of the elevation direction E as a center.

Figure 5:
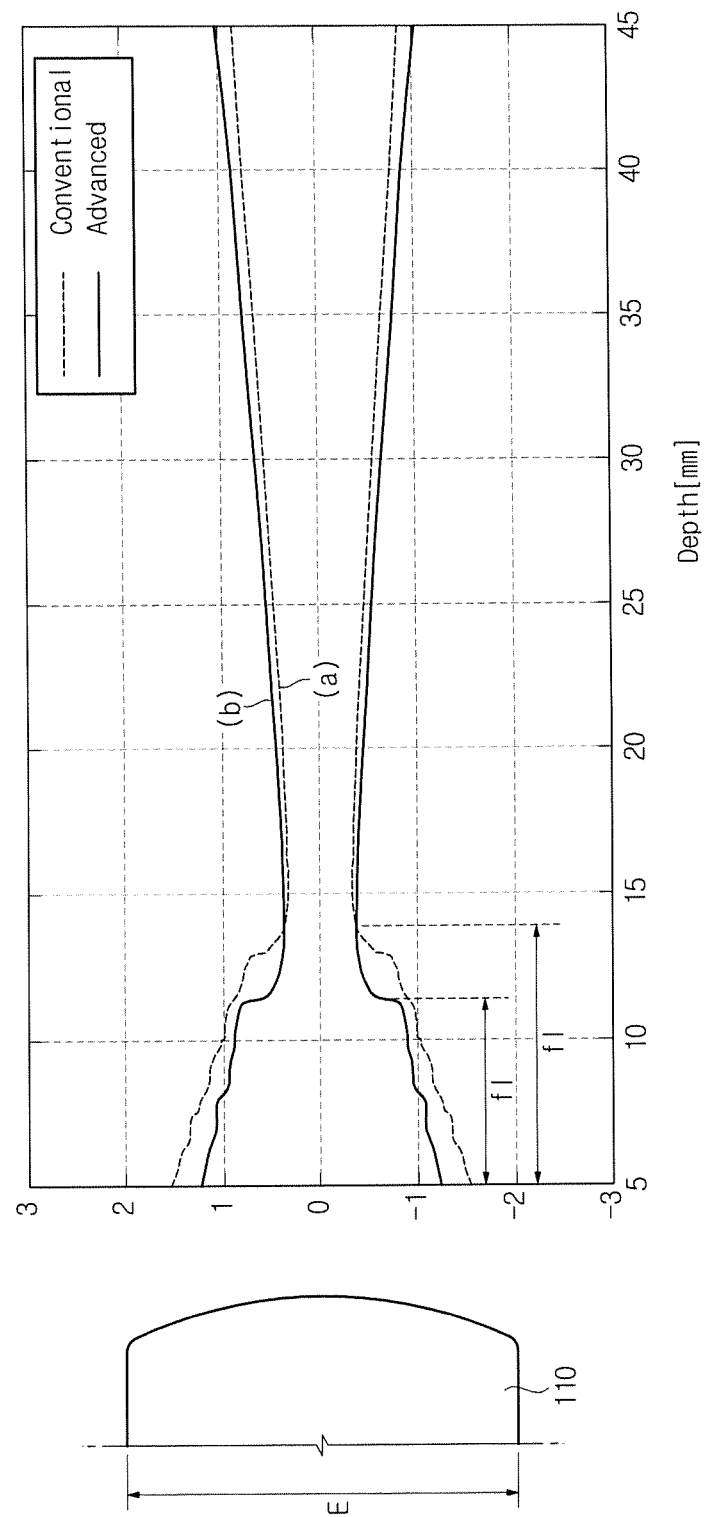
FIG. 5 is an illustration with respect to width of beams of ultrasonic waves transmitted from the transducer module in accordance with an exemplary embodiment.

FIG. 5 is an illustration with respect to width of beams of ultrasonic waves transmitted from the transducer module in accordance with one exemplary embodiment.

In a case of using the reflective layer 113 in accordance with the embodiments of FIG. 3 and FIG. 4 ((b) on FIG. 5), as illustrated on FIG. 5, the focusing length fl of the ultrasonic waves transmitted may be decreased when compared to (a) of FIG. 5, and the band of the ultrasonic waves having large acoustic pressure strength with respect to a predetermined acoustic pressure strength at a short-distance domain may be narrowly formed.

In addition, in a case of using the reflective layer 113 in accordance with the embodiments of FIG. 3 and FIG. 4, the less-needed side lobe of the elevation direction E at a short-distance domain may be reduced.

Hereinafter, by referring to FIG. 6, a manufacturing method of the transducer module 110 in accordance with one embodiment of the present disclosure will be described.

Figure 6:
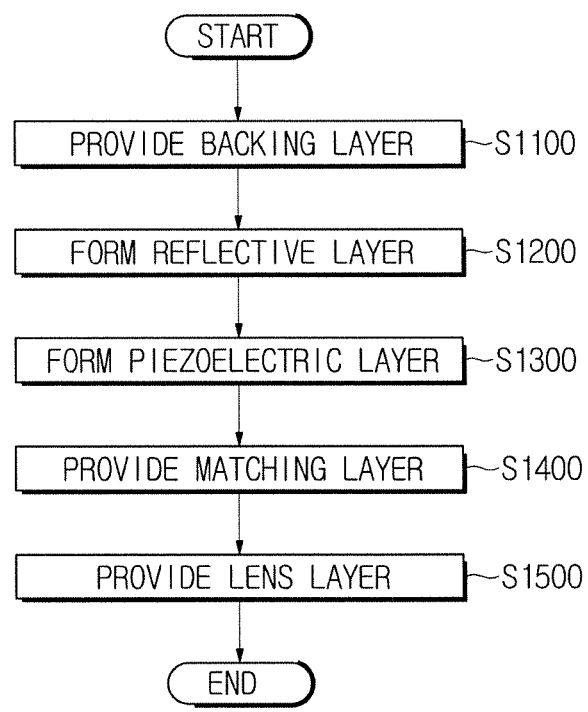
FIG. 6 is a flow chart of a manufacturing method of the transducer module in accordance with an exemplary embodiment.

FIG. 6 is a flow chart of the manufacturing method of the transducer module in accordance with one exemplary embodiment.

First, the backing layer is provided first (S1100).

Next, the reflective layer 113 partially covering an upper surface of the backing layer 112 is formed (S1200).

In the case as the above, the reflective layer 113 may be formed at a first depressed surface of the backing layer 112, as the first depressed surface is formed by partially removing the backing layer 112.

The area of the first depressed surface or the length of the elevation direction E of the backing layer 112 may be provided to be small or shorter with respect to the area or the elevation direction E of the piezoelectric layer 111, which is to be provided later.

In the case as the above, the reflective layer 113 may be provided at the central portion of the piezoelectric layer 111 in the elevation direction E so as to occupy a short length in the elevation direction E, for example, less than about 90% of the piezoelectric layer 111.

The height of the depressed surface of the backing layer may be varied depending on the structure provided at an inside the removed backing layer 112. For example, in a case when the reflective layer 113 is provided at an inside the backing layer 112, the height of the depressed surface of the backing layer 112 may be identical with respect to the height of the reflective layer 113.

However, in a case when the reflective layer 113 and the piezoelectric layer 111 are provided at an inside the backing layer 112, the height of the depressed surface of the backing layer 112 may be identical with respect to the sum of the height of the reflective layer 113 and the height of the piezoelectric layer 111.

The reflective layer 113 may be provided with large acoustic impedance with respect to the piezoelectric layer 113. For example, the reflective layer 113 may be provided with material having the acoustic impedance that is about 1.5 times greater than the acoustic impedance of the piezoelectric layer 111, for example, between about 50 MRayl and about 150 MRayl.

Meanwhile, the embodiment described earlier is described that, after the backing layer 112 is provided, the reflective layer 113 is provided, but the order of such is not limited hereto, and the backing layer 112 may be provided by molding or adhesively attaching the backing layer 112 at a lower surface of the reflective layer 113 after the reflective layer 113 is provided.

Next, the piezoelectric layer 111 covering an upper surface of the reflective layer 113 is formed (S1300).

In accordance with one embodiment of the present disclosure, the piezoelectric layer 111 may be provided as to cover an upper surface of the reflective layer 113 and an upper surface of a non-compressed surface of the backing layer 112. That is, the piezoelectric layer 111 may be stacked at an upper surface of the reflective layer 113 and at an upper surface of the backing layer 112. In the case as such, the height of the depressed surface of the backing layer 112 is formed to be identical with respect to the height of the reflective layer 113, and the area or the length of the elevation direction E of the piezoelectric layer 111 may be small or identical with respect to the area or the length of the elevation direction E of the backing layer 112.

In accordance with another embodiment of the present disclosure, the piezoelectric layer 111 may be provided as to cover the upper surface of the second depressed surface of the backing layer 112, which is generated by partially removing the backing layer 112, and the upper surface of the reflective layer 113. In the case as such, the height of the depressed surface of the backing layer 112 is formed to be identical to the sum of the height of the reflective later 113 and the height of the piezoelectric layer 111, and the area or the length of the elevation direction E of the piezoelectric layer 111 may be small with respect to the area or the length of the elevation direction E of the backing layer 112.

Meanwhile, the embodiment described earlier is described that, after the reflective layer 113 is provided, the piezoelectric layer 111 is provided, but the order of such is not limited hereto, and the reflective layer 113 may be provided by molding or adhesively attaching the reflective later 113 at a lower surface of the piezoelectric layer 111 after the piezoelectric layer 111 is provided.

Next, the lens layer 115 covering an upper surface and a side surface of the piezoelectric layer 111 is provided (S1500). The lens layer 115 may be formed by use of material having strong wear resistance and high ultrasonic wave frequency, for example, aluminum, as to focus ultrasonic waves and perform a role to protect piezoelectric layer 111. The lens layer 115 may be provided with the shape that is convex toward a radiating direction of ultrasonic waves as to focus the ultrasonic waves, and in a case when acoustic speed is slower than a human body, the lens layer 115 may be provided with a concave shape. Further, the matching layer 114 may be provided between the piezoelectric layer 111 and the lens layer 115 (S1400).

In the embodiment of the present disclosure, one unit of the lens layer 115 formed at the probe is described as an example. However, the plurality of lens layers 115 provided with the each lens layer 115 having different material property with respect to each other may be formed at the probe.

In accordance with one aspect of the present disclosure, by providing a reflective layer occupying a smaller area than a piezoelectric layer at a probe, the focusing length of ultrasonic waves can be reduced, and the bandwidth of the ultrasonic waves having acoustic pressure greater than a predetermined strength of acoustic pressure at a short-distance domain can be formed to be narrow.

In addition, in accordance with another aspect of the present disclosure, a side lobe of focused beams can be reduced.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A probe, comprising:
   a piezoelectric layer to generate ultrasonic waves;
   a backing layer to absorb ultrasonic waves generated at the piezoelectric layer and proceeding toward a rear;
   a reflective layer occupying an area smaller than an area of the piezoelectric layer and provided in between the piezoelectric layer and the backing layer to amplify the ultrasonic waves generated at the piezoelectric layer; and
   a lens layer to focus the ultrasonic waves proceeding toward a front of the piezoelectric layer at a certain point.

2. The probe of claim 1, wherein:
   the reflective layer is configured to be provided at a central portion in an elevation direction of the probe.

3. The probe of claim 1, wherein:
   the reflective layer is configured to be formed of material having am acoustic impedance higher than an acoustic impedance of the piezoelectric layer.

4. The probe of claim 1, wherein:
   the reflective layer is configured to be formed of material having an acoustic impedance 1.5 times higher than an acoustic impedance of the acoustic impedance of the piezoelectric layer.

5. The probe of claim 1, further comprising:
   a matching layer to reduce a difference of acoustic impedances between the piezoelectric layer and a subject.

6. The probe of claim 1, wherein:
   the reflective layer is configured to be provided at a depressed surface of the backing layer.

7. The probe of claim 1, wherein:
   the piezoelectric layer and the reflective layer are configured to be provided at the depressed surface of the backing layer.

8. The probe of claim 1, wherein:
   the reflective layer is configured to occupy a shorter length in the elevation direction than a length of the piezoelectric layer.

9. The probe of claim 1, wherein:
   the piezoelectric layer, the backing layer, the reflective layer, and the lens layer each is configured to be provided with both end portions thereof symmetrical to each other about a central portion of the probe having a length in the elevation direction.

* * * * *